(12) United States Patent
Johnson et al.

(10) Patent No.: US 9,125,955 B2
(45) Date of Patent: Sep. 8, 2015

(54) $^{99m}$TC IMAGING AGENTS AND METHODS OF USE

(71) Applicant: GENERAL ELECTRIC COMPANY, Schenectady, NY (US)

(72) Inventors: Bruce Fletcher Johnson, Scotia, NY (US); Randall Lee Carter, Clifton Park, NY (US); Michael James Rishel, Saratoga Springs, NY (US); Mark Christopher Patrick Darey, Charleston, WV (US); Tao Wu, Ancaster (CA); Yang Yang, Edmonton (CA); John Fitzmaurice Valliant, Ancaster (CA); Karin Ann Stephenson, Burlington (CA)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/072,846

(22) Filed: Nov. 6, 2013

(65) Prior Publication Data
US 2014/0065065 A1    Mar. 6, 2014

Related U.S. Application Data

(62) Division of application No. 13/362,658, filed on Jan. 31, 2012, now abandoned.

(51) Int. Cl.
| | |
|---|---|
| *A61K 51/04* | (2006.01) |
| *A61K 51/06* | (2006.01) |
| *A61K 51/08* | (2006.01) |
| *A61K 38/00* | (2006.01) |
| *A61K 51/10* | (2006.01) |

(52) U.S. Cl.
CPC ........... *A61K 51/1093* (2013.01); *A61K 51/04* (2013.01); *A61K 51/0474* (2013.01); *A61K 51/0491* (2013.01); *A61K 51/08* (2013.01); *A61K 51/088* (2013.01)

(58) Field of Classification Search
CPC ....... A61K 51/04; A61K 51/06; A61K 51/08; A61K 38/00
USPC ........... 424/1.49, 1.65, 1.69, 9.1, 9.36, 9.365, 424/1.11; 562/18, 34, 157, 212, 253, 367, 562/368
See application file for complete search history.

(56) References Cited

U.S. PATENT DOCUMENTS

| | | | |
|---|---|---|---|
| 5,395,608 | A | 3/1995 | Troutner et al. |
| 5,688,487 | A | 11/1997 | Linder et al. |
| 5,997,843 | A | 12/1999 | Archer et al. |
| 6,254,850 | B1 | 7/2001 | Krause et al. |
| 6,270,745 | B1 | 8/2001 | Duatti et al. |
| 6,534,038 | B2 | 3/2003 | Liu |
| 7,049,289 | B1 | 5/2006 | Storey et al. |
| 7,445,765 | B2 | 11/2008 | Duatti et al. |
| 7,597,875 | B2 | 10/2009 | Archer et al. |
| 8,022,211 | B2 | 9/2011 | Bhalla |

FOREIGN PATENT DOCUMENTS

| | | |
|---|---|---|
| EP | 0738158 B1 | 4/2002 |
| EP | 1404377 B1 | 9/2005 |
| WO | 2004037297 A1 | 5/2004 |
| WO | WO-2004/037297 * | 5/2004 |

OTHER PUBLICATIONS

Bartholomä et al., "Technetium and Gallium Derived Radiopharmaceuticals: Comparing and Contrasting the Chemistry of Two Important Radiometals for the Molecular Imaging Era", Chem. Rev., vol. 110, pp. 2903-2920, 2010.

Liu, "Bifunctional Coupling Agents for Radiolabeling of Biomolecules and Target-Specific Delivery of Metallic Radionuclides", Advanced Drug Delivery Reviews, vol. 60, pp. 1347-1370, 2008.

Jurisson et al., "Effect of Ring Size on Properties of Technetium Amine Oxime Complexes. X-Ray Structures of TcO2Pent(AO)2, Which Contains an Unusual Eight-Membered Chelate Ring, and of TcOEn(AO)2", Inorg. Chem., vol. 26, No. 21, pp. 3576-3582, 1987.

Lo et al., "Chemical Characteristics of 99mTc-Labeled Amine Oximes", Appl. Radiat. Isot., vol. 44, No. 8, pp. 1139-1146, 1993.

Alberto et al., Comprehensive Coordination Chemistry II, Pergamon, Oxford, pp. 127-270, 2003, ISBN 9780080437484, 10.1016/B0-08-043748-6/04022-6. (http://www.sciencedirect.com/science/article/pii/B0080437486040226).

Schwochau, "Technetium: Chemistry and Radiopharmaceutical Applications", John Wiley & Sons, Ltd., pp. 1-226, 2000.

Search Report and Written Opinion from corresponding PCT Application No. PCT/EP2013/051874 dated Jul. 26, 2013.

* cited by examiner

*Primary Examiner* — Michael G Hartley
*Assistant Examiner* — Jagadishwar Samala
(74) *Attorney, Agent, or Firm* — Eileen B. Gallagher

(57) ABSTRACT

An embodiment of the invention comprises method of imaging a target site comprising administrating ligand of Formula I complexed to $^{99m}$Tc

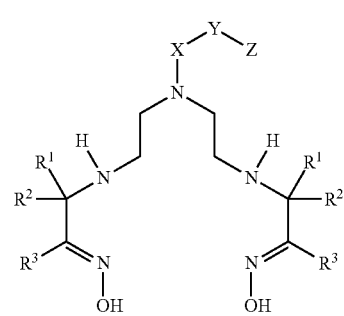

wherein $R^1$ and $R^2$ are independently an alkyl or cycloalkyl; $R^3$ is and alkyl; X is CO or $SO_2$; Y is $(CH2)_n$, $C_6H_4$, $(OCH_2CH_2)_n(NHCH_2CH_2)_n$ and $(OCH_2CH_2CH_2)_n$, or a combination thereof; Z is linker group capable of conjugating to a vector; and n is an integer between 0 and 10.

6 Claims, 5 Drawing Sheets

99mTC IMAGING AGENTS AND METHODS OF USE

CROSS-REFERENCE TO RELATED APPLICATIONS

This application is a divisional of U.S. application Ser. No. 13/362,658, filed on Jan. 31, 2012, and is copending. The entire disclosure of U.S. application Ser. No. 13/362,658 is incorporated herein by reference.

BACKGROUND

The invention relates to imaging agents and methods for SPECT, and more particularly to imaging agents radiolabeled with $^{99m}$Tc.

The most widely used radionuclide in nuclear medicine is technetium-99m ($^{99m}$TC; $T_{1/2}$=6.0 h, 140 KeV γ emission). While the majority of clinically approved $^{99}$Tc-radiopharmaceuticals are perfusion-type agents (diagnostic images of blood flow), there is a growing interest to develop and commercialize single photon emission computed tomography (SPECT) imaging agents that target specific biomarkers.

Exploitation of this opportunity requires the creation of ligand which acts as a technetium chelator to incorporate $^{99m}$Tc and is capable of regioselectively conjugating to a variety of vectors, including biomolecules. Vectors refer to a vehicle used to transfer material to a target or target site. Ideally, the ligand should be capable of incorporating $^{99m}$Tc without impairing the biological properties of the vector.

While ligands capable of chelating with $^{99m}$Tc are well known, few ligands meet the criteria needed to develop an effective agent. For example in certain synthetic methodologies $^{99m}$Tc incorporation is achieved under basic conditions, which can be deleterious to certain peptides/proteins.

For example European Patent EP0738158 and U.S. Pat. No. 7,597,875 disclose a ligand with an all-carbon bridge and shown in FIG. 1 (structure A). The ligand (A) is capable of conjugation a broad array of vectors via the primary nitrogen. However, like diaminodioximes in general it requires a pH of approximately 9-10 to label optimally. This pH is incompatible with many sensitive biomolecules. Furthermore the synthesis of the structure A yields mono, bi, and tri functionalized products from which the desired bi-functionalized chelate must be isolated by preparative HPLC.

U.S. Pat. No. 7,049,289 discloses a ligand, (FIG. 1, structure B), that may also be appropriate for conjugation a broad array of vectors via the primary nitrogen; it is also synthetically more accessible than the all carbon backbone (structure A). However as taught in U.S. Pat. No. 7,597,875, this ligand does not form a single radiolabeled species with $^{99m}$Tc under mild conditions.

Similarly, U.S. Pat. No. 5,688,487 and U.S. Pat. No. 5,997,843 disclose a ligand, (FIG. 1, structure C) with an all carbon bridge and nitroimidazole vector (X) attached at the C1 position. This construct is limited in that it is not easy for a facile and broad conjugation to vectors as the vector is incorporated early in a multistep synthesis.

As such, the development of an alternative approach involving chelation that is effective at slightly basic to acidic pH and is readily synthesized would provide a technology to enable technetium radiolabeling of vectors without pH limitations. Furthermore it would be desirable to have $^{99m}$Tc incorporation in a single step in a manner suitable for clinical production of agents with high effective specific activity. Accordingly, there is a need for imaging systems and methods that can provide a high resolution, high sensitivity image in a shorter period of time and which may be produced under mild aqueous conditions.

BRIEF DESCRIPTION

An embodiment of the invention comprises a ligand of Formula I

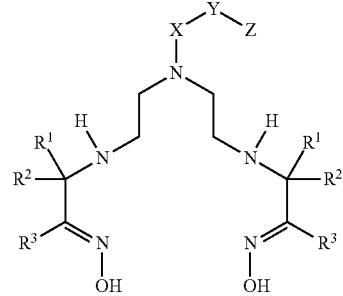

wherein $R^1$ and R2 are independently an alkyl or cycloalkyl; $R^3$ is an alkyl; X is CO or $SO_2$, Y is $(CH_2)_n$, $C_6H_4$, $(OCH_2CH_2)_n$, $(NHCH_2CH_2)_n$ and $(OCH_2CH_2CH_2)_n$ or a combination thereof; Z is linker group capable of conjugating to a vector; and n is an integer between 0 and 10.

In one embodiment, an imaging agent comprising a compound of Formula I complexed to $^{99m}$Tc.

Another embodiment of the invention comprises administering to a subject having a target site, an imaging agent comprising a ligand, complexed with $^{99m}$Tc, and chemically bound to a vector through a linker moiety, and wherein the ligand comprises a compound of Formula I. An example of the method generally comprises, allowing the imaging agent to localize to the target site; and detecting the imaging agent at the target using single photon emission computed tomography (SPECT).

DRAWINGS

These and other features, aspects, and advantages of the present invention will become better understood when the following detailed description is read with reference to the accompanying drawings in which like characters represent like parts throughout the drawings, wherein.

DEFINITIONS

The present invention may be understood more readily by reference to the following detailed description of preferred embodiments of the invention and the examples included therein. In the following specification and the claims which follow, reference will be made to a number of terms which shall be defined to have the following meanings:

In the context of the present invention, alkyl is intended to include linear, branched, or cyclic hydrocarbon structures and combinations thereof, including lower alkyl and higher alkyl. Preferred alkyl groups are those of C20 or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Figure 1:
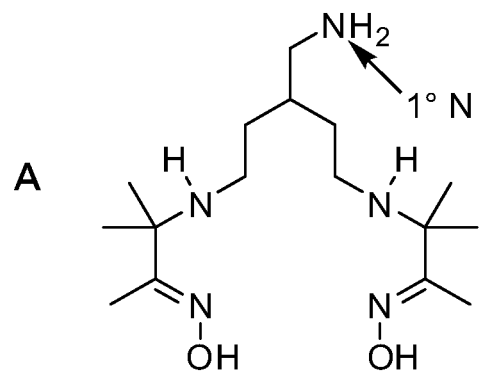
FIG. 1 are structures of ligands capable of chelating with $^{99m}$Tc.
Figure 1:
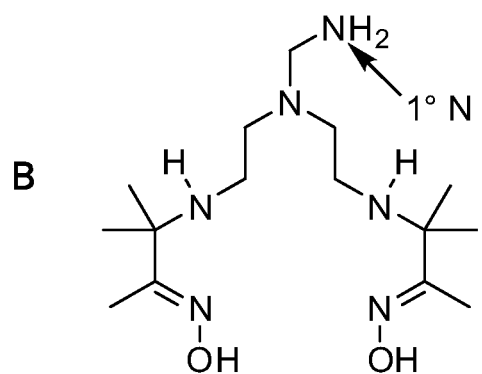
Figure 1:
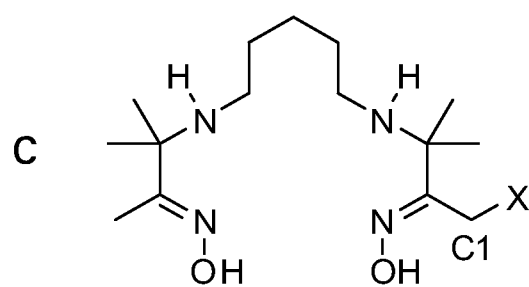
Figure 2:
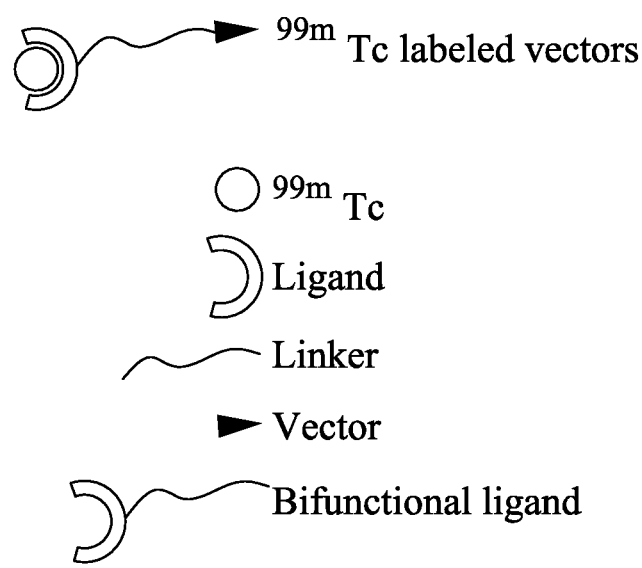
FIG. 2 is a schematic representation of the $^{99m}$Tc-ligand complex.

DETAILED DESCRIPTION $^{99m}$Tc labeled vectors are of great interest for molecular imaging via SPECT and their basic configuration as illustrated in FIG. 1. As shown, a ligand acts as a technetium chelator to incorporate $^{99m}$Tc while binding to a vector through a linker moiety. The vector is a biologically active molecule which affects the biodistribution of the $^{99m}$Tc by binding to targets, or target sites, such as receptors or enzymes associated with specific tissues, lesions or pathological processes. This enables the presence or absence of these receptors to be imaged noninvasively via single-photon emission computed tomography (SPECT). The vector can be a small molecule, peptide or biomacromolecule such as an antibody. The ligand is critical for linking the $^{99m}$Tc to vector. A schematic representation of the $^{99m}$Tc-ligand complex is shown in FIG. 2

Imaging agents for use in the compositions and methods of the present invention include structural units derived from a ligand represented by Formula I

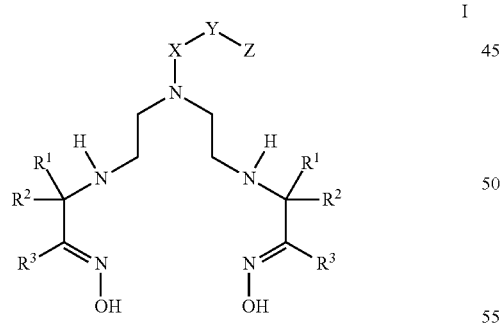

I wherein $R^1$ and $R^2$ are independently an alkyl or cycloalkyl;
$R^3$ is an alkyl;
X is CO or $SO_2$;
Y is $(CH_2)_n$, $C_6H_4$, $(OCH_2CH_2)_n(NHCH_2CH_2)_n$ and $(OCH_2CH_2CH_2)_n$ or a combination thereof;
Z is a group capable of conjugating to a vector; and
n is an integer between 0 and 10.

Ligands of Formula I have a tertiary nitrogen which makes this class of ligands more synthetically accessible than their counterparts lacking the nitrogen. Furthermore the electron withdrawing properties of X may facilitate the complexation of Formula I with $^{99m}$Tc by making the tertiary nitrogen less able to participate in binding to the Tc which allows only one species to form. As such, using the ligands of Formula I as part of a radiolabeled molecular imaging agents, provide a means of incorporating a broad array of vectors useful in a wide variety of diagnostic and therapeutic monitoring applications In certain embodiments, $R^1$, $R^2$, and $R^3$ are independently lower alkyl groups. In certain other embodiments, $R^1$, $R^2$, and $R^3$ are $CH_3$, X is $SO_2$, Y is a direct bond such that n is 0, and Z is linker group capable of conjugating to a vector.

Figure 3:
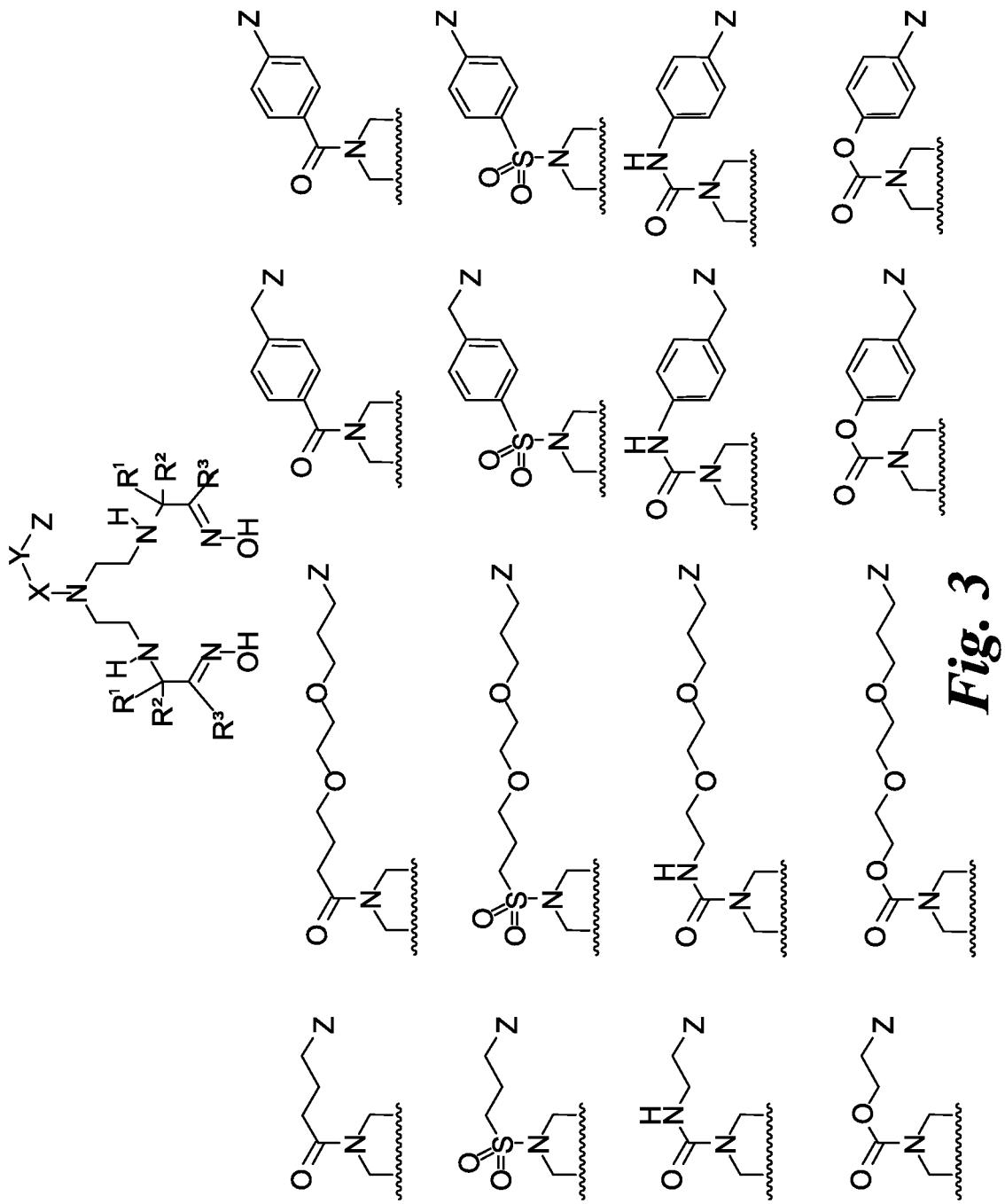
FIG. 3 is a schematic representation of examples of the "N—X—(Y)$_n$—Z" structure of Formula I.

Exemplary structures of the "N—X—Y—Z moiety of Formula I are shown in FIG. 3.

In certain embodiments the Z group, includes a moiety that attaches or conjugates the ligand to the vector. Example of linkers include, but are not limited to, carboxylic acids, activated esters, such as N-hydroxysuccinimide ester or pentafluorophenyl ester, phosphoramidite, isocyanate, isothiocyanate, aldehyde, acid chloride, sulfonyl chloride, alkyl halide, amine, phosphine, phosphate, alcohol, thiol, or a combination thereof.

Exemplary ligands include, but are not limited to,

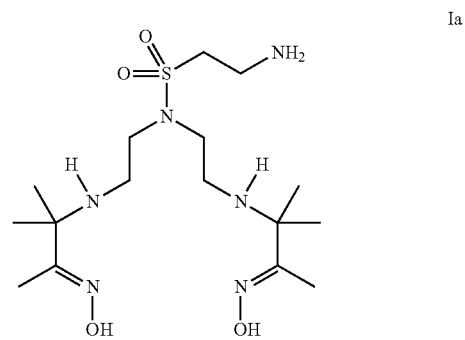

Ia

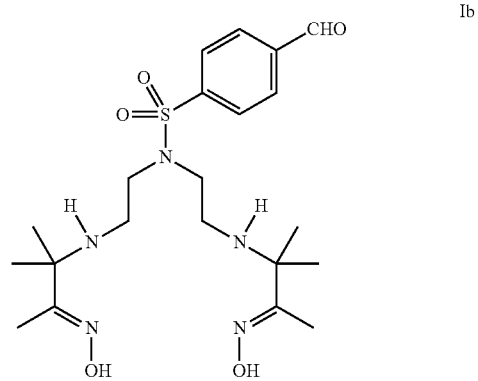

Ib

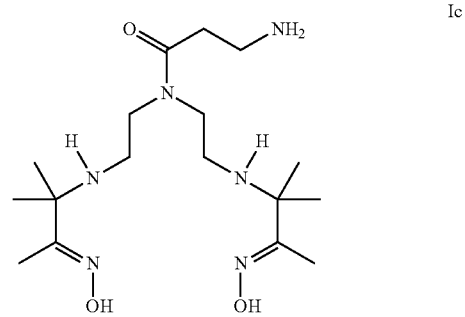

Ic

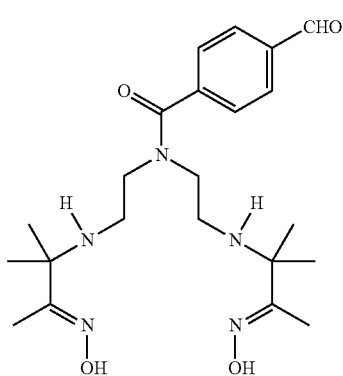

Id

In certain embodiment the ligand of Formula I is chemically bound to a vector through a linker moiety The vector is a compound that differentially accumulates in a target site. A site may be a cell, group of cells, organ, tumor or lesion relative to nearby sites. The accumulation of the vector in the target site may be due to the vector binding to and/or interaction with a biomarker that is differentially expressed at the target site relative to nearby sites. Representative examples of biomarkers include, but is not limited to human epidermal growth factor receptor 2 (HER-2) brain thymidine kinase 1 (TK-1), and peripheral benzodiazepine receptors (PBRs).

Non-limiting examples of vectors includes small molecules, proteins, peptides, polypeptides, glycoproteins, lipoproteins, phospholipids, oligonucleotides, steroids, alkaloids or the like, e.g., hormones, lymphokines, growth factors, albumin, cytokines, enzymes, immune modulators, receptor proteins, oligonucleotides or mimics thereof, and antibodies and antibody fragments, individually or in any combination thereof as well as derivatives thereof. In certain embodiments the vectors may be classified as 3-100 mer peptides or peptide analogues which may be linear peptides or cyclic peptides or combinations thereof; monoclonal antibodies or fragments thereof; or enzyme substrates or inhibitors; synthetic receptor-binding compounds; oligonucleotides, or oligo-DNA or oligo-RNA fragments. The vectors may be of synthetic or natural origin. Examples of particular vectors include aptamers and thioaptamers. Preferred vectors are 3-20 mer peptides. Examples of vectors, which may also be referred to as a "biological targeting moiety" may be found in U.S. Pat. No. 7,597,875 entitled "Chelator Conjugates" and issued Oct. 6, 2009. The patent is hereby incorporated by reference.

In certain embodiments, $R^1$, $R^2$, and $R^3$ are independently lower alkyl groups. In certain other embodiments, $R^1$, $R^2$, and $R^3$ are $CH_3$, X is $SO_2$, Y is a direct bond wherein n is 0, and Z is linker.

In certain embodiments the Z group, includes a moiety that attaches or conjugates the ligand to the vector. Example of linkers include, but are not limited to, carboxylic acids, activated esters, such as N-hydroxysuccinimide ester or pentafluorophenyl ester, phosphoramidite, isocyanate, isothiocyanate, aldehyde, acid chloride, sulfonyl chloride, alkyl halide, amine, phosphine, phosphate, alcohol, thiol, or a combination thereof.

In certain embodiments, the ligand of Formula I is complexed with $^{99m}$Tc to form a radiolabel. The complexation chemistry of $^{99m}$Tc may be produced by using different methods. In certain methods it is produced using pertechnetate $^{99m}$TcO$_4$-requiring reduction and complexation using the reduced state. The trans dioxo $^{99m}$TCO$_2^+$ core may also be used and has the advantage of being symmetrical around the Tc core when complexed.

In certain embodiments the complexation of the ligand of Formula I with $^{99m}$Tc may be depicted as Formula II. Wherein the $^{99m}$Tc complexes of the chelators are neutral, Tc(V) dioxo complexes:

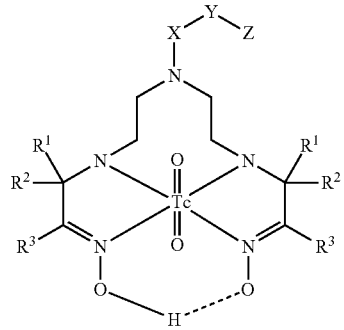

II wherein $R^1$ and $R^2$ are independently an alkyl or cycloalkyl;

$R^3$ is and alkyl;

X is CO or $SO_2$;

Y is $(CH_2)_n$, $C_6H_4$, $(OCH_2CH_2)_n(NHCH_2CH_2)_n$ and $(OCH_2CH_2CH_2)_n$ or a combination thereof;

Z is linker group capable of conjugating to a vector; and n is an integer between 0 and 10.

In certain embodiments, a target may be detected by administering to a subject an imaging agent comprising the ligand of Formula I, complexed with $^{99m}$Tc and chemically bound to a vector through a linker moiety, allowing the imaging agent to travel to the target site via intracellular diffusion and to subsequently bind to the target of interest thorough noncovalent or covalent (rare) association. The pattern of accumulated agent is detected in the subject using SPECT. For example, for some applications the labeled may be detected in cancerous cells wherein the ligand binds to a biomarker such as Human Epidermal growth factor Receptor 2 (HER2) which is overexpressed in certain breast cancers.

Figure 4:
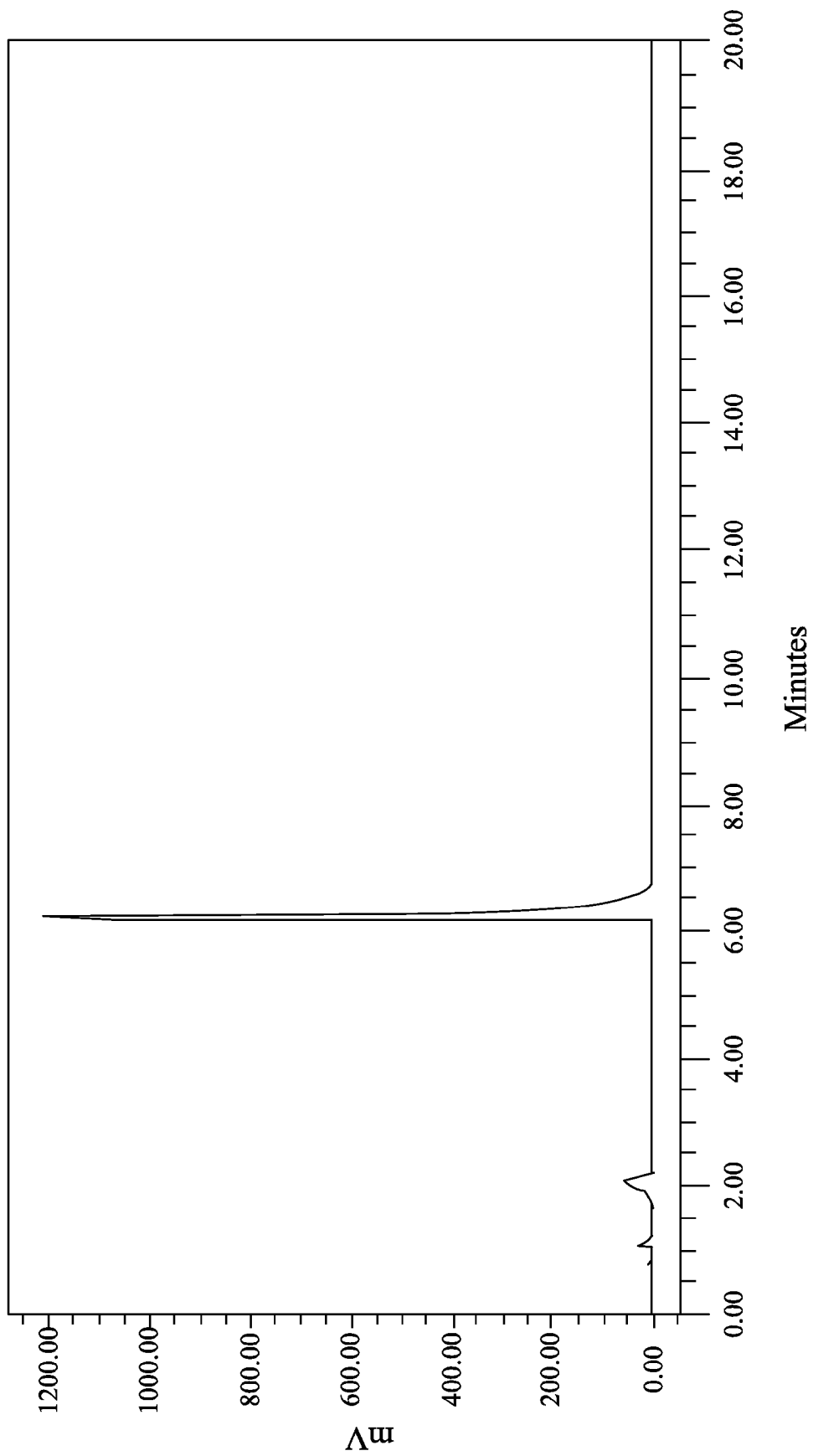
FIG. 4 is graph representing HPLC analysis of Formula 2.

In certain embodiments, the imaging agent may be dissolved or suspended in a pharmaceutical carrier to allow for administering the imaging agent to a subject. Pharmaceutical carrier refers to a composition which allows the application of the agent material to the site of the application, surrounding tissues, or prepared tissue section to allow the agent to have an effective residence time for specific binding to the target or to provide a convenient manner of release. Formulation strategies may include but are not limited to: pH adjustments, salt formation, formation of ionizable compounds, use of co-solvents, complexation, surfactants and micelles, emulsions and micro-emulsions. The pharmaceutical carrier may include, but is not limited to, a cosolvent, detergent, buffer solution, stabilizers, and preservatives. Examples of these include but are not limited to, HCl, citric acid, DMSO, propylene glycol, ethanol PEG 300, cyclodextrans, citrate, acetate, phosphate, carbonate or tris(hydroxymethyl)aminomethane. Particularly, the pharmaceutical carrier is suitable for intravenous, intramuscular, subcutaneous, or parenteral administration (e.g., by injection). These pharmaceuticals may also be administered orally under appropriate circumstances Experimental Complexation with $^{99m}$Tc may be accomplished while maintaining a solution pH of about 6 to about 10 and more preferable a pH of about 7 to about 9. This is depicted in the experimental results shown in FIG. 4, whereby the radiolabeling of Formula 2

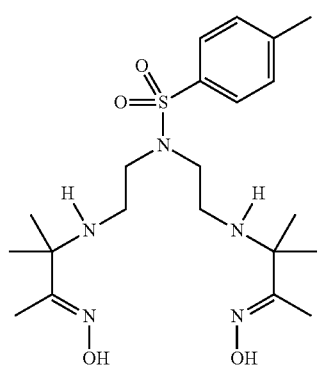

2 was achieved at pH 9 and 7~7.5 in 15 min in 1/1 (v/v) DMSO/H$_2$O as evidenced by HPLC analysis of retention time (minutes) vs. response (mV).

In each case, with or without the use of a common co-ligand used in $^{99m}$Tc radiolabelling, good radiochemical purity (RCP) was achieved and colloid formation was minimal (Table 1). Noteworthy is the high RCP that occurred at pH 7-7.5 which addresses the need for a mild pH conditions. The co-ligand used was methylenediphosphonic acid (MDP).

TABLE 1

$^{99m}$Tc (V) Labeling of 2 at pH 9 and 7-7.5.

| pH | MDP | % RCP | Colloid | Activity | Rxn Time |
|---|---|---|---|---|---|
| 9 | yes | 96% | 0.33% | 0.24 GBq (6.6 mCi) | 15 min |
| 9 | no | 95% | 1.06% | 0.27 GBq (7.2 mCi) | 15 mm |
| 7~7.5 | yes | 94% | 1.19% | 0.28 GBq (7.6 mCi) | 15 min |

Figure 5:
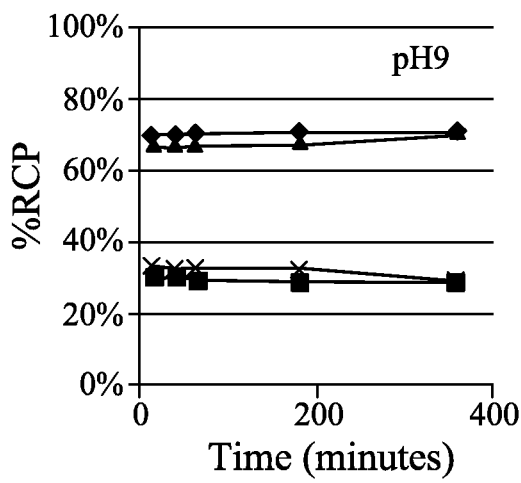
FIG. 5 are graphical representations of competition experiments comparing Structure C (X=H) (FIG. 1) and Formula 2 at different pH values.
Figure 5:
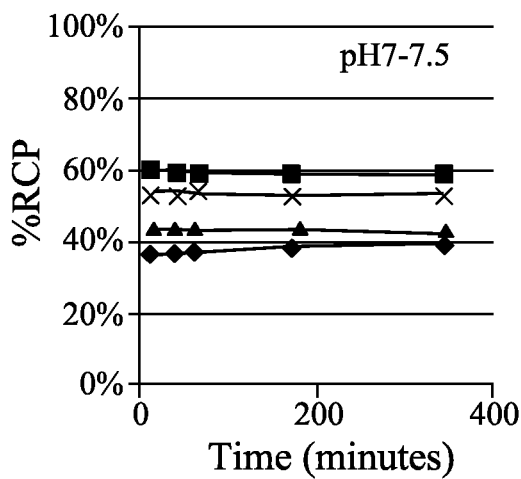
Figure 5:
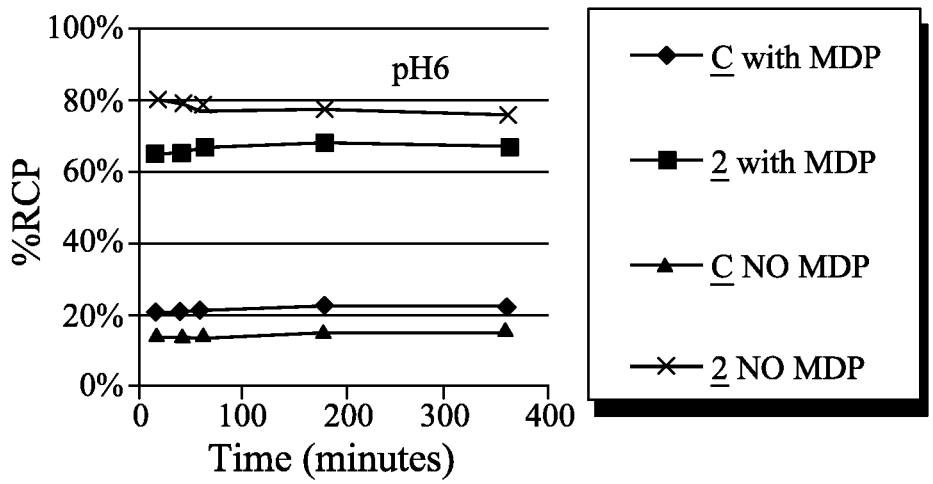

Competition experiments between structure C (X=H) (FIG. 1) and Formula 2, were carried out at pH 9, 7~7.5 and 6. Results are presented in FIG. 5 which shows radiochemical purity (RCP) as a percentage vs. time (minutes) for a range of pH values. At pH 9, the complexation of C was still dominating regardless the presence of MDP (C/2 product ratio ~3:1). However, at lower pH (7~7.5), the complex of 2 became the major product (product ratio ~1:1.5). At even lower pH (6), 2 showed a higher complexation amount than C (product ratio ~1:3). The results demonstrate improved performance of 2 relative to C as pH is reduced.

Reaction amounts are given in tables. Often a reagent will list a volume and weight; this means that the reagent was dispensed by volume but the amount determined by weight. All calculations are based on weight.

Synthesis of Diaminedioxime C(X=H)

Diaminedioxime C(X=H) has been shown to cleanly form a complex with $^{99m}$Tc that forms a dioxo TcO$_2$$^+$ core.

3-chloro-3-methyl-2-butanone oxime 20

The chloroxime was synthesized following the procedure from European Patent Application EP404377 filed Apr. 6, 2009.

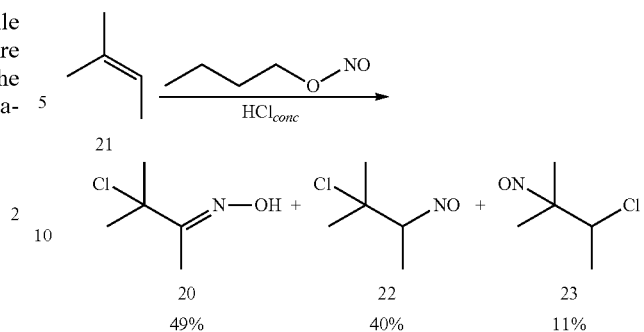

TABLE 2

| | purity w/w | MW g/mol | amt g | amt mmol | eq | d g/ml | vol ml | CA # |
|---|---|---|---|---|---|---|---|---|
| 21 | 100% | 70.1 | 33.15 | 470 | 1.24 | 0.66 | 50.0 | 513-35-9 |
| isoamyl nitrite | 98% | 117.2 | 46.22 | 379 | 1.00 | 0.87 | 50.0 | 110-46-3 |
| HCl conc | 37% | 36.5 | 56.5 | 574 | 1.51 | 1.19 | 47.5 | |
| EtOH | | | 34 | | | | ml | |
| 20 | 95% | 135.6 | 33.4 | 234 | 62% | yield | | 3238-16-2 |

2-methyl-2-butene 21 was mixed with isoamyl nitrite and cooled to −70° C. in a MeOH/dry ice bath. HCl$_{conc}$ was added over 50 min., keeping the temperature between −30 and −20° C. EtOH (34 mL) was added towards the end of the addition, but the mixture still solidified to a gel after the addition was complete. The batch was stirred for a further 2 h. at −20 to −10° C., then filtered (filtration and washes took about 40 min.). The filter cake was washed with chilled EtOH (40 mL) followed by ice-cold water (50 mL) and was left to dry for 90 min. The wet weight was 66.4 g. After drying under vacuum, the weight fell to 33.4 g (0.246 moles, 62% theory). Proton NMR indicated that the product (now a mixture of viscous liquid and solid) was a mixture of the trans-oxime 20 (49%), nitroso-tautomer 22 (40%) and 3-nitroso-2-chlorobutane 23 (11%). Upon storing in the refrigerator, the material solidified yielding the trans-oxime 20.

3,3'-(1,5-pentanediyldiimino)bis[3-methyl-2-butanone]dioxime C(X=H)

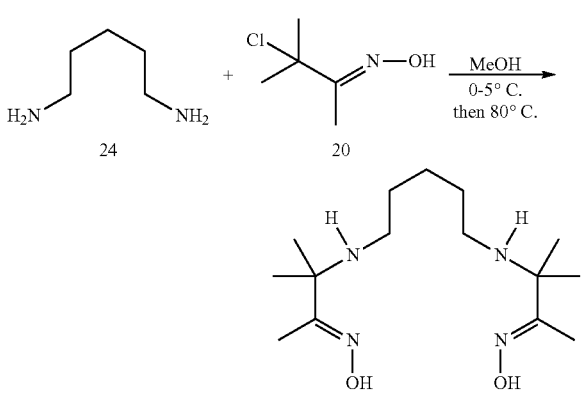

TABLE 3

| | purity w/w | MW g/mol | amt g | amt mmol | eq | d g/ml | vol ml | CA # |
|---|---|---|---|---|---|---|---|---|
| 22 | 95% | 135.6 | 9.40 | 66 | 2.29 | | | 3238-16-2 |
| 24 | 95% | 102.2 | 3.10 | 29 | 1.00 | 0.87 | 3.55 | 462-94-2 |
| MeOH | | | 40 | ml | | | | |
| C | 95% | 300.4 | 0.638 | 2 | 7.0% | yield | | 109929-73-9 |

Chloroxime 20 was dissolved in MeOH (40 mL) to give a pale green solution. The solution was cooled to below 0° C. in an ice/acetone bath, and a white solid precipitated. 1,5-diaminopentane 24 was added over about 30 m, keeping the temperature below 0° C. (initial exotherm to 10° C.). On commencing the addition, the mixture became an orange brown color, turning to a thin dark violet slurry by the end of the addition. The mixture was stirred at room temperature overnight. TLC in $CH_2Cl_2$/MeOH/$NH_3$ and visualization with ninhydrin stain showed that the mixture consisted of two major components: one very polar (presumably monoalkylated) and one less polar (presumably dialkylated). Heating to reflux for 2 h. did not appear to change the composition of the mixture. Water (100 mL) was added to the cooled mixture, and 0.9 g of a yellow solid was collected by filtration. The pH of the filtrate was adjusted to pH 12, whereupon a viscous oil partitioned from the aqueous layer. The oil was extracted into $CH_2Cl_2$, and the organic layer concentrated to give 8 g of a purple gum. The gum was further dried under vacuum over night at room temperature, to give 6 g of a sticky solid. The solid was triturated with water (75 mL) and filtered to give 4 g of dirty white solid, which was still slightly sticky. The solid was dissolved in refluxing MeOH (20 mL) and cooled in an ice/water bath over 90 min. The white solid was collected by filteration, and dried under vacuum to give 638 mg (2.1 mmol, 7% theory) of the desired ligand as a white solid. MS, $^1$H and $^{13}$C NMRs confirmed the structure. In this procedure a Hunig's base was not used but may be added Synthesis of Formula 2

N,N-bis[2-[(phenylsulfonyl)oxy]ethyl]-benzene-sulfonamide 18

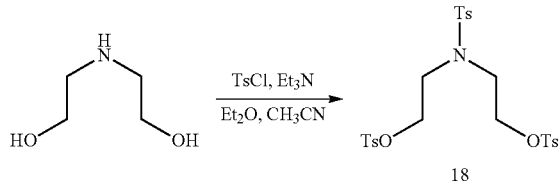 [SMILES: OCCNCCO ; Cc1ccc(S(=O)(=O)OCCN(CCOS(=O)(=O)c2ccc(C)cc2)S(=O)(=O)c2ccc(C)cc2)cc1]

TABLE 4

| | purity w/w | MW g/mol | amt g | amt mmol | eq | d g/ml | vol ml | CA # |
|---|---|---|---|---|---|---|---|---|
| diethanolamine | 98% | 105.1 | 4.0 | 37.3 | 1.00 | | | 111-42-2 |
| TsCl | 98% | 190.7 | 23.5 | 120.8 | 3.24 | | | 616-47-7 |
| Et3N | 100% | 101.2 | 13.2 | 130.4 | 3.50 | 0.726 | 18 | 121-44-8 |
| Et2O | | | | 120 | ml | | | |
| CH3CN | | | | 100 | ml | 261 | reaction volume | |
| 18 | 95% | 567.7 | 13.8 | 23.1 | 62% | yield | | 22185-13-3 |

Et$_3$N in 20 mL of Et$_2$O was added to tosyl chloride in 100 mL Et$_2$O in a 500 mL flask. This was stirred and cooled in an ice bath. Diethanolamine was melted in an oven and transferred to a 100 ml flask, 80 mL of CH$_3$CN was added to the amine to dissolve it, and the mixture was added via cannula to the mixture of tosylchloride and Et$_3$N to form a white suspension. The progress of the reaction was monitored via HPLC.

The reaction was worked up after 5 days by evaporating the solvent under an active stream on nitrogen gas. Diethylether was added to the residue to produce a suspension and the precipitate was collected by filtration. The precipitate was purified on a gravity silica gel column starting with 60/40 hexanes/CH$_2$Cl$_2$ progressing to 100% CH$_2$Cl$_2$.

N,N-bis(2-aminoethyl)-4-methyl-benzenesulfonamide 19

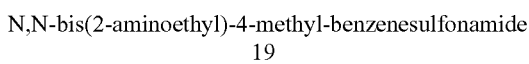
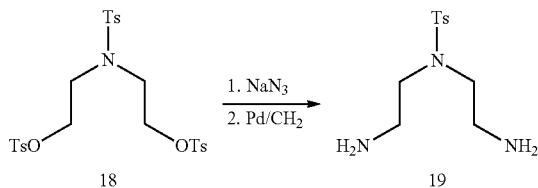 [SMILES: Cc1ccc(S(=O)(=O)OCCN(CCOS(=O)(=O)c2ccc(C)cc2)S(=O)(=O)c2ccc(C)cc2)cc1 ; Cc1ccc(S(=O)(=O)N(CCN)CCN)cc1]

TABLE 5

| | purity w/w | MW g/mol | amt g | amt mmol | eq | CA # |
|---|---|---|---|---|---|---|
| 18 | 95% | 567.7 | 6.25 | 10.5 | 1.00 | 22185-13-3 |
| NaN3 | 99% | 65.0 | 2.12 | 32.2 | 3.08 | 26628-22-8 |
| DMF | | | 102 | ml | | |
| 10% Pd/C | 10% | 106.4 | 0.36 | 0.3 | 0.03 | |
| EtOH | | | 102 | ml | | |
| 19 | 95% | 257.4 | 0.87 | 3.2 | 31% yield | 23539-15-3 |

Compound 18 (6.25 g) and NaN$_3$ (2.115 g) in 102 mL DMF was heated at 100° C. for 2 h. After this time, HPLC indicated that the reaction was complete. The reaction mixture was allowed to cool, and 10% K$_2$CO$_{3aq}$ solution (100 mL) was added. The mixture was extracted 3 times with hexanes (60 mL) but most of the azide separated out as an interphase solid, which was dissolved in CH$_2$Cl$_2$. EtOH (100 mL) was added and the solution concentrated to 100 mL. Pd/C catalyst (0.36 g) was added, the flask flushed with N$_2$, then evacuated and flushed with H$_2$ (from a balloon). The reaction was stirred under H$_2$ for 3 hr, after which HPLC indicated that no starting material remained. The reaction mixture was filtered and concentrated to give 1.7 g of pale yellow oil (60% theory). The oil was dissolved in water and then was purified by chromatography on C-18 (10 g, 60 mL). The column was first flushed with CH$_3$CN, then with water/0.05% TFA. The crude solution was loaded onto the column, and was eluted with water (35 mL), followed by water/CH$_3$CN 98:2 (20 mL), then 20 mL fractions in which the percentage of CH$_3$CN was increased by 2% each time, up to 16%. Fractions 2-11 contained pure diamine by HPLC and were concentrated, to give 1.3 g of a sticky white solid. After drying under vacuum, the weight fell to 0.87 g (31% theory).

N,N-bis(2-((E)-3-(hydroxyimino)-2-methylbutan-2-ylamino)ethyl)-4-methylbenzenesulfonamide 2

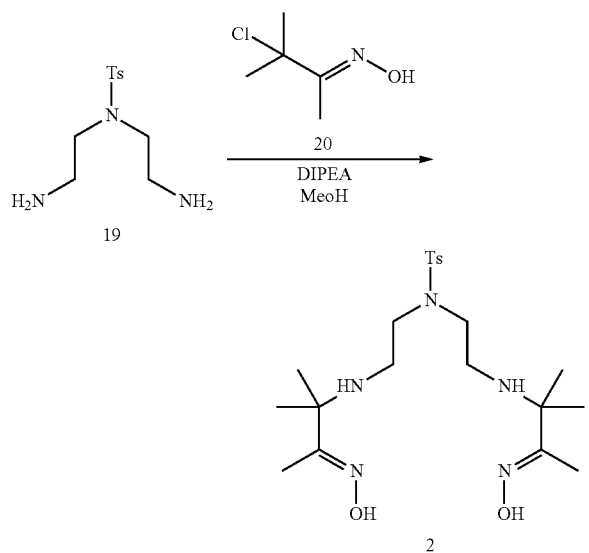

TABLE 6

| | purity w/w | MW g/mol | amt g | amt mmol | eq | d g/ml | ml | CA # |
|---|---|---|---|---|---|---|---|---|
| 19 | 95% | 257.4 | 0.85 | 3.1 | 1.0 | | | 22185-13-3 |
| 20 | 95% | 135.6 | 3.60 | 25.2 | 8.0 | | | 3238-16-2 |
| DIPEA | 99% | 129.2 | 3.40 | 26.0 | 8.3 | 0.742 | 4.60 | 7087-68-5 |
| EtOH | | | | 20 ml | | | | |
| 2 | 95% | 455.6 | 0.535 | 1.1 | 36% | yield | | |

Tosyl diamine 19 (850 mg) was slurried with EtOH and cooled in an ice water bath to 0-5° C. A total of 3.4 g DIPEA (diisopropylethylamine) and 3.6 g of 20 were added in 3 portions over about 3 hours after which time HPLC showed that no free diamine remained. The reaction mixture was concentrated, water (40 mL) was added, and the solution acidified with 1.5 mL $HCl_{conc}$. The aqueous layer was extracted with 2×50 mL $CH_2Cl_2$. The pH of the aqueous layer was then adjusted to 10 with $K_2CO_3$ (a precipitate formed). The aqueous layer was extracted with $CH_2Cl_2$ which was concentrated and slurried with MeOH. The dialkylated product was collected by filtration as a white solid. Dry weight was 535 mg (36% theory).

Radiolabeling

Ligand stability studies: A stock solution (prepared by dissolving ~300 μg of ligand in 4 mL of water; in the cases of Compound 2, 4 mL of DMSO/$H_2O$[1:1 v/v] was used) was stored on bench top at room temperature without extra precautions. LC-MS was taken every 24 h and no decomposition was observed after 3 days.

General labeling procedure (pH 9): To a 10 mL vial containing 0.21 mL of cpn ligand (3) stock solution (16 μg, 75 μg/mL, aq.), 200 μL of NaOAc (4 mg, 20 mg/mL, aq.), 0.5 mL of pH 9 bicarbonate buffer and 13.2 μL of MDP (13.2 μg, 1.0 mg/mL, aq.), were added 1 mL of $Na^{99m}TcO_4^-$ solution and 14.3 μL of $SnCl_2.2H_2O$ (36 μg, 2.51 mg/mL, aq.), sequentially. The pH value of the reaction solution was measured by a pH strip and verified to be pH 9. The reaction mixture was allowed to sit at room temperature for 15 min. At the end of the experiment, the pH value was measured again with a pH strip, and the reaction solution was filtered through a filter (Acrodisc® 13 mm Syringe filter with 0.2 μm Nylon Membrane, HPLC Certified filter, Pall corporation, N.Y.) on the tip of a 5 mL syringe. 2 mL of water was pushed through the filter followed by the measurement of radioactivities of combined filtrate, filter, original vial, syringe and needle. An aliquot of the filtrate was subjected to HPLC analysis.

General labeling procedure (pH 7~7.5, $NaHCO_3$ buffer): To a 10 mL vial containing 0.21 mL of cpn ligand (3) stock solution (16 μg, 75 μg/mL, aq.), 0.15 mL of 100 mM $NaHCO_3$ solution (pH 8.0-8.5) and 13.2 μL of MDP (13.2 μg, 1.0 mg/mL, aq.), were added 1 mL of $Na^{99m}TcO_4^-$ solution and 14.3 μL of $SnCl_2.2H_2O$ (36 μg, 2.51 mg/mL, aq.), sequentially. The pH value of the reaction solution was measured to be 7~7.5 (by a pH strip) and the reaction mixture allowed to sit at rt for 15 min. At the end of the experiment, the pH value was measured again with a pH strip, and the reaction solution was filtered through a filter (Acrodisc® 13 mm Syringe filter with 0.2 μm Nylon Membrane, HPLC Certified filter) on the tip of a 5 mL syringe. 2 mL of water was pushed through the filter followed by the measurement of radioactivities of combined filtrate, filter, original vial, syringe and needle. An aliquot of the filtrate was subjected to HPLC analysis.

General labeling procedure (pH 7-7.5): The above general procedure was adopted with the following changes: pH value of the solution was adjusted to 7 to 7.5 by the addition of a 0.1 N NaOH solution after the addition of $SnCl_2$.

General labeling procedure (pH 6): To a 10 mL vial containing 0.42 mL of cpn ligand (3) stock solution (32 μg, 75 μg/mL, aq.), 0.025 mL of 100 mM $NaHCO_3$ solution (pH 8.0-8.5) and 13.2 μL of MDP (13.2 μg, 1.0 mg/mL, aq.), were added 1.21 mL of $Na^{99m}TcO_4^-$ solution and 14.3 μL of $SnCl_2.2H_2O$ (36 μg, 2.51 mg/mL, aq.), sequentially. The pH value of the reaction solution was measured to be ~6 (by a pH strip) and the reaction mixture was allowed to sit at rt for 15 min. At the end of the experiment, the pH value was measured again with a pH strip, and the reaction solution was filtered through a filter (Acrodisc® 13 mm Syringe filter with 0.2 μm Nylon Membrane, HPLC Certified filter) on the tip of a 5 mL syringe. 2 mL of water was pushed through the filter followed by the measurement of radioactivities of combined filtrate, filter, original vial, syringe and needle. An aliquot of the filtrate was subjected to HPLC analysis.

Analytical Methods HPLC conditions: All analytical studies were performed on Waters Acquity UPLC system. Column: Waters Acquity Analytical UPLC column (100×2.1 mm, C18, 1.7 μm BEH. Mobile Phase: solvent A is 0.4% ammonium formate in $H_2O$ and solvent B is acetonitrile.

TABLE 7

| Flow rate: 0.3 ml/min | | | | | | |
|---|---|---|---|---|---|---|
| Time (mins) | 0 | 3 | 10 | 15 | 16 | 20 |
| % B | 10 | 10 | 75 | 75 | 10 | 10 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of imaging a target site comprising:
administering to a subject having a target site, an imaging agent comprising a ligand, complexed with $^{99m}$Tc, and chemically bound to a vector through a linker moiety, and wherein said ligand comprises a compound of Formula I

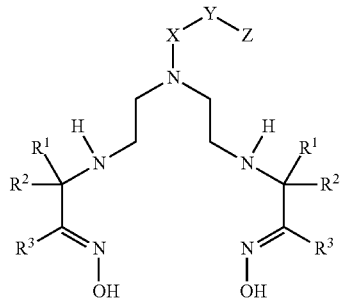

$R^1$, $R^2$, and $R^3$ are $CH_3$;
X is $SO_2$;
Y is $CH_2$;
Z is linker group capable of conjugating to a vector; and
n is 1;
allowing the imaging agent to localize to the target site; and
detecting the imaging agent at the target using single photon emission computed tomography (SPECT).

2. The method of claim 1 wherein Z comprises carboxylic acid, an activated ester, a phosphoramidite, isocyanate, isothiocyanate, aldehyde, acid chloride, sulfonyl chloride, alkyl halide, amine, phosphine, phosphate, alcohol, thiol, or a combination thereof.

3. The method of claim 2 wherein the activated ester comprises N-hydroxysuccinimide ester, pentafluorophenyl ester, or a combination thereof.

4. The method of claim 1 wherein the vector comprises 3-100 mer peptides or peptide analogues, monoclonal antibodies or fragments thereof; enzyme substrates, enzyme inhibitors; synthetic receptor-binding compounds, oligonucleotides, oligo-DNA fragments, oligo-RNA fragments, or a combination thereof.

5. The method of claim 4 wherein the vector comprises a 3-100 mer peptide, peptide analogues, or combinations thereof.

6. A method of imaging a target site comprising:
administering to a subject having a target site, an imaging agent comprising a ligand, complexed with $^{99m}$Tc, and chemically bound to a vector through a linker moiety, wherein said ligand comprises

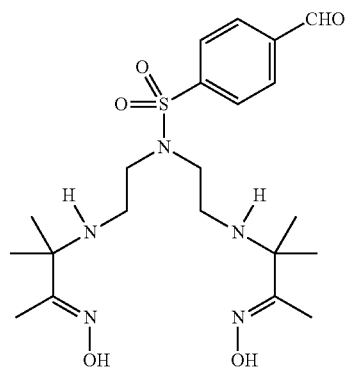 [SMILES: C/C(=N\O)C(C)(C)NCCN(CCNC(C)(C)/C(C)=N/O)S(=O)(=O)c1ccc(C=O)cc1]

allowing the imaging agent to localize to the target site; and
detecting the imaging agent at the target using single photon emission computed tomography (SPECT).

* * * * *